US009039990B2

(12) United States Patent
Storberg (10) Patent No.: US 9,039,990 B2
(45) Date of Patent: May 26, 2015

(54) VENTILATOR AUTOCLAVE (75) Inventor: Bengt Storberg, Falkenberg (SE)

(73) Assignee: GETINGE STERILIZATION AB, Getinge (SE)

( * ) Notice: Subject to any disclaimer, the term of this patent is extended or adjusted under 35 U.S.C. 154(b) by 487 days.

(21) Appl. No.: 13/138,857

(22) PCT Filed: May 7, 2009

(86) PCT No.: PCT/SE2009/050500
§ 371 (c)(1),
(2), (4) Date: Oct. 11, 2011

(87) PCT Pub. No.: WO2010/128907
PCT Pub. Date: Nov. 11, 2010

(65) Prior Publication Data
US 2012/0039766 A1 Feb. 16, 2012

(51) Int. Cl.
*A61L 2/04* (2006.01)
*A61L 2/07* (2006.01)
(Continued)

(52) U.S. Cl.
CPC ............... *A61L 2/07* (2013.01); *A61L 2202/10* (2013.01)

(58) Field of Classification Search
CPC ....... A61L 2/0011; A61L 2/0023; A61L 2/04; A61L 2/06; A61L 2/07
USPC .......... 422/292, 300, 307, 293, 295, 297, 302
See application file for complete search history.

(56) References Cited

U.S. PATENT DOCUMENTS

| 2,093,334 A | 9/1937 | Meitzler |
| 4,935,604 A | 6/1990 | Allen et al. |

FOREIGN PATENT DOCUMENTS

| CN | 2934312 | 8/2007 |
| DE | 4100436 A1 | 7/1992 |
| JP | S58-101641 U | 7/1983 |

(Continued)

OTHER PUBLICATIONS

English machine translation of JP 09-239009, Sep. 16, 1997.*

(Continued)

*Primary Examiner* — Regina M Yoo
(74) *Attorney, Agent, or Firm* — Harness, Dickey & Pierce, P.L.C.

(57) ABSTRACT

The present invention relates to a ventilator autoclave comprising a chamber (1) with a space (5) for receiving goods (18) to be sterilized, at least one fan arrangement (2) for circulating steam and/or air in said chamber, and at least one first heat exchanger arrangement (11) for cooling and/or heating said steam and/or air, wherein said fan arrangement is arranged and configured to circulate said steam and/or air in said chamber (1), wherein said chamber (1) is configured such that said steam and/or air that is circulated in said chamber (1) follows a flow path passing at least a part of said first heat exchanger arrangement (11) before reaching said goods (18) to be sterilized, wherein said autoclave further comprises at least one second heat exchanger arrangement (19) that is provided upstream of said first heat exchanger arrangement (11) in said flow path, and wherein said second heat exchanger arrangement (19) is provided at such a distance from the periphery of said fan arrangement (2) that said flow of steam and/or air being circulated by said fan arrangement has a tangential velocity component, as seen in relation to the fan arrangement, when it passes said second heat exchanger arrangement (19).

20 Claims, 3 Drawing Sheets (51) Int. Cl.
*A61L 2/00* (2006.01)
*A61L 9/00* (2006.01)

(56) References Cited

FOREIGN PATENT DOCUMENTS

| JP | 09-239009 | | 9/1997 |
|----|-----------|---|--------|
| JP | 2000-116757 | | 4/2000 |
| JP | 2002-010965 | | 1/2002 |
| JP | 2003-135574 | | 5/2003 |
| UA | 65058 | A | 3/2004 |
| WO | WO-96/22795 | A1 | 8/1996 |
| WO | WO-00/64494 | A1 | 11/2000 |

OTHER PUBLICATIONS

English machine translation of JP 2002-010965, Jan. 15, 2002.*
English machine translation of JP 2000-116757, Apr. 25, 2000.*
English machine translation of JP 2003-135574, May 13, 2003.*
Mar. 15, 2013 Japanese Office Action issued in Japanese Patent Application No. 2012-509755 (translation).
Chinese Office Action dated Jun. 3, 2013 issued in corresponding Chinese Appln. No. 200980159029.1 (English translation).
European Search Report issued Apr. 24, 2014 in corresponding European Application No. 09844434.
Chinese Office Action dated Feb. 17, 2014 issued in corresponding Chinese Appln. No. 200980159029.1.

* cited by examiner

VENTILATOR AUTOCLAVE

CROSS REFERENCE TO RELATED APPLICATION

The present application is a national stage application under 35 U.S.C. §371 of International Application No. PCT/SE2009/050500, filed May 7, 2009 with the World Intellectual Property Organization.

FIELD OF THE INVENTION

The present invention relates to a ventilator autoclave comprising a chamber with a space for receiving goods to be sterilized, at least one fan arrangement for circulating steam and/or air in said chamber, and at least one first heat exchanger arrangement for cooling and/or heating said steam and/or air, wherein said fan arrangement is arranged and configured to circulate said steam and/or air in said chamber, wherein said chamber is configured such that said steam and/or air that is circulated in said chamber follows a flow path passing at least a part of said first heat exchanger arrangement before reaching said goods to be sterilized.

BACKGROUND OF THE INVENTION

Preparation of e.g. injectable medications and intravenous solutions requires a high sterility level to reduce or eliminate the risk of exposing persons and animals to microorganisms, such as bacteria and viruses. A widely used device for sterilization of pre-filled containers is the so called ventilator or steam/air autoclave. Ventilator autoclaves are autoclaves where air is kept in the sterilization chamber during the process, unlike traditional steam sterilizers in which air is removed before sterilization. The purpose of maintaining air in the sterilization chamber is to provide a supporting pressure that assists in avoiding deformation of the containers.

Known ventilator autoclaves often comprise a sterilization chamber, a fan for circulating the steam/air in the chamber and heat exchangers for heating/cooling the steam/air. The fan may e.g. be a centrifugal fan and is often installed at the top of the sterilization chamber. The heat exchangers are commonly placed along the side walls of the chamber, behind internal panels that creates a duct between the internal panel and the autoclave wall. By this, a circulating environment is created in which the fan directs steam/air towards the heat exchangers. When steam/air passes the heat exchangers it is heated or cooled, depending on the phase of the sterilization process, before it is directed towards the goods in the autoclave.

In general terms, the sterilization process is carried out in the following manner. The goods to be sterilized, e.g. in the form of pre-filled plastic syringes, containers and vials comprising liquid, gel-like or paste-like pharmaceutical or biological products are typically placed in the autoclave. Heating liquid may then optionally be supplied to the heat exchangers so that the air in the autoclave becomes heated and pre-heats the goods to be sterilized. Thereafter, the goods to be sterilized is subjected to steam until the temperature reaches about 121° C. This temperature is maintained for a time sufficient to sterilize the content. As the prefilled container is heated, the fluid or formulation contained therein vaporizes. The vapor produces a pressure and temperature which is lethal or cidal to pathogens. Following sterilization, the pre-filled containers are subjected to a cooling step. During the cooling step, cooling liquid is supplied to the heat exchangers, which in turn cool the steam/air in the autoclave.

The known ventilator autoclaves are known to function well. However, as in many industrial processes, there are economic benefits if the sterilization process may be carried out faster. Hence, it is an object of the present invention to suggest an improved ventilator autoclave that may be able to carry out the sterilization process faster than known autoclaves.

SUMMARY OF THE INVENTION

An improved ventilator autoclave is defined in claim 1. Said ventilator autoclave comprises a chamber with a space for receiving goods to be sterilized, at least one fan arrangement for circulating steam and/or air in said chamber, and at least one first heat exchanger arrangement for cooling and/or heating said steam and/or air, wherein said fan arrangement is arranged and configured to circulate said steam and/or air in said chamber, wherein said chamber is configured such that said steam and/or air that is circulated in said chamber follows a flow path passing at least a part of said first heat exchanger arrangement before reaching said goods to be sterilized, wherein said autoclave further comprises at least one second heat exchanger arrangement that is provided upstream of said first heat exchanger arrangement in said flow path, and wherein said second heat exchanger arrangement is provided at such a distance from the periphery of said fan arrangement that said flow of steam and/or air being circulated by said fan arrangement has a tangential velocity component, as seen in relation to the fan arrangement, when it passes said second heat exchanger arrangement.

The flow of steam and/or air that exits a radial fan usually has both a tangential and a radial velocity component and close to the periphery of the fan, the tangential velocity component is substantial. Hence, the flow may be considered to have a spiral-shaped pattern around the fan. The tangential velocity component usually decreases the further away from the fan the steam/air has moved and hence, the speed of the flow also decreases the further away from the fan the steam/air has moved. If the speed of the flow is lower, each molecule of the flow of steam/air will be in contact with a heat exchanger for a longer time, which likely would provide a more effective heat exchanging effect.

However, it has surprisingly been found that the effect of a heat exchanger is increased if the heat exchanger is positioned so that the steam and/or air that passes it has both a tangential and a radial velocity component while passing through the heat exchanger. The reason for this is that the spiral-shaped pattern of movement will increase the distance the steam and/or air is in contact with the heat exchanger, as compared to the situation where the flow of steam and/or air is essentially radial. Hence, the steam and/or air will come into contact with a larger area of the heat exchanger. This increases the heat exchanging effect even though the speed of the steam and/or air is higher when the flow has a tangential velocity component, i.e. closer to the fan.

Hence, providing a second heat exchanger arrangement to the ventilator autoclave and positioning the second heat exchanger so that the steam and/or air that is being circulated by said fan has a tangential velocity component when it passes said second heat exchanger improves the cooling or heating of the steam and/or air in the autoclave. By providing a more effective cooling or heating process, the time required for the sterilization cycle may be shortened, which gives economic benefits to the user of the ventilator autoclave.

According to one exemplary embodiment, said at least one fan arrangement is provided at the ceiling of said chamber. According to one exemplary embodiment, said autoclave comprises two first heat exchanger arrangements, which are provided adjacent at least two of said chamber's opposite side walls.

The fan is preferably a radial, or in other words, a centrifugal fan provided at the ceiling of the autoclave chamber. Such a fan may then draw air from the chamber and direct it towards the side walls of the chamber where the first heat exchangers may be provided. The second heat exchanger may e.g. be provided above the first heat exchangers on the respective side walls of the chamber or at the ceiling of the chamber. By that, a circulating flow path may be created in the autoclave chamber, in which the flow of air and/or steam first passes the second heat exchanger and thereafter the first heat exchanger before it reaches the goods to be sterilized.

The position of the first heat exchangers along the side walls of the chamber has the effect that the flow of steam and/or air is essentially radial when it passes the first heat exchangers.

According to one exemplary embodiment, said autoclave comprises at least one partition wall, wherein said partition wall separate the space for receiving goods to be sterilized from the space where said first heat exchanger arrangement is provided.

By this arrangement, a wall of the chamber and a partition wall provide a duct along the wall of the chamber. The flow path in which the steam and/or air is moved from said fan and passes said first heat exchanger or heat exchangers before it reaches said goods is then physically separated from the space for receiving goods to be sterilized. There may be provided an opening between the partition wall and the floor of the chamber so that the steam and/or air may exit the duct and enter the space for goods to be sterilized close to the bottom of the chamber. The steam and/or air may thereafter pass the goods to be sterilized in a substantially vertical direction, before it once again is drawn into the fan and circulated towards the first and second heat exchangers.

In the embodiment with the first heat exchangers provided along two of the side walls of the chamber, there may be provided partition walls along both of the sides as well. By that, a duct is provided along both of the side walls of the chamber.

According to one exemplary embodiment, said second heat exchanger arrangement is provided at the ceiling of said chamber.

The second heat exchanger should be provided upstream of the first heat exchanger in the flow path and close enough to the fan so that the flow has a tangential component when it passes it. One alternative is then to provide it at the ceiling of the chamber.

The second heat exchanger may be provided in alternative manners. According to one exemplary embodiment, the second heat exchanger comprises several horizontally provided pipes, which may contain heating or cooling liquid. According to another exemplary embodiment, the second heat exchanger comprises several horizontally placed plates, which may contain heating or cooling liquid.

According to one exemplary embodiment, said second heat exchanger arrangement is provided so that it circumscribes said fan arrangement. By this arrangement, all steam and/or air that exits the fan will have to pass through the second heat exchanger and be cooled or heated depending on the phase of the sterilization process. When the steam and/or air has passed the second heat exchanger, it will follow the flow path towards the first heat exchangers.

According to other exemplary embodiments, the second heat exchanger may be provided so that it circumscribes only a portion of said fan arrangement. For example, the second heat exchanger may be provided so that it circumscribes e.g. 60-80% of said fan arrangement. Furthermore, the second heat exchanger arrangement may be provided as e.g. two or three separate heat exchangers that are mutually distanced and provided circumferentially around said fan. Each one of the second heat exchangers may then span approximately 90-110° of a circle circumscribing said fan.

In either one of the embodiments where the second heat exchanger comprises a number of horizontally placed pipes or plates, the uppermost pipe or plate may be in contact with the ceiling of the chamber. The lowermost pipe or plate may be provided at approximately the same height as the lowermost portion of the fan.

According to one exemplary embodiment, said second heat exchanger arrangement is provided at a distance of 0-25 cm from the periphery of said fan arrangement, more preferably at a distance of 2-12 cm from the periphery of said fan arrangement and most preferred at a distance of 3-7 cm from the periphery of said fan arrangement.

According to one exemplary embodiment, said second heat exchanger arrangement is provided at a distance from the periphery of said fan arrangement that corresponds to 0-50% of the diameter of said fan arrangement, more preferred 4-25% of the diameter of said fan arrangement and most preferred 6-14% of the diameter of said fan arrangement.

When the steam and/or air is brought into circulation by the fan, it exits the fan with both a tangential and a radial velocity component, i.e. the steam and/or air moves in what may be seen as a spiral shaped pattern around the fan. This tangential velocity component decreases with the distance the steam and/or air moves and after a certain distance, the steam and/or air moves with essentially only a radial velocity component in relation to the fan. The decreasing rate is in turn dependent on the speed of the steam and/or air as it exits the fan.

It has, as mentioned above, been surprisingly found that providing the second heat exchanger so that the flow of air and/or steam has a tangential velocity component when it passes the heat exchanger provides a more effective cooling or heating of the steam and/or air, even though the speed of the flow of steam and/or air is higher as compared to a position further away from the fan. The ranges given above has proven to be beneficial distances between the periphery of the fan, where the steam and/or air exits the fan, and the second heat exchanger, i.e. with these distances, the steam and/or air will have a tangential velocity component when it passes the second heat exchanger.

In the embodiment where the second heat exchanger circumscribe said fan, the distances mentioned above is meant to be the distance between the periphery of the fan and the side of the heat exchanger that is closest to the fan.

According to one exemplary embodiment, said autoclave comprises partition walls, wherein said partition walls separates the space for receiving goods to be sterilized from the space where said first heat exchanger arrangement is provided, wherein said partition walls are provided with slots, through which a partial or total flow of steam and/or air may be diverted.

By this arrangement, a wall of the chamber and a partition wall provide a duct along the wall of the chamber. The flow path in which the steam and/or air is moved from said fan to said first heat exchanger before it reaches said goods is then physically separated from the space for receiving goods to be sterilized. There may in certain embodiments also be provided an opening between the partition wall and the floor of the chamber so that the steam and/or air may exit the duct and enter the space for goods to be sterilized close to the bottom of the chamber. The steam and/or air may thereafter pass the goods to be sterilized in a substantially vertical direction, before it once again is drawn into the fan and circulated towards the first and second heat exchangers.

However, in certain sterilization processes it may be beneficial to utilize also a horizontal flow of steam and/or air towards the products to be sterilized. In that case, a partial or total amount of the flow of steam and/or air may be diverted through the slots provided in the partition wall. Due to the provision of the first heat exchanger, with its surprising cooling and heating effect, even the steam and/or air being diverted from the duct with the first heat exchangers before it has passed any of the complete first heat exchanger arrangements, will provide a sufficient cooling or heating effect on the goods to be sterilized.

In one exemplary embodiment, there is provided so that the opening between the partition wall and the bottom of the chamber may be closed. By this, it is possible to ensure, for those applications where a substantially horizontal flow is desired, that the total flow of steam and/or air exits the duct in which the first heat exchanger is provided through the slots in the partition wall.

According to one exemplary embodiment, said slots are provided at different heights along the partition walls, wherein a partial flow of steam and/or air may be diverted at different heights in said chamber.

The goods to be sterilized are often placed at carriers that may hold goods at different heights, i.e. the carriers use as much of the volume of the space for goods to be sterilized as possible. By providing slots at different heights along the partition wall or walls, some or all of the steam and/or air may exit the duct or ducts and pass the goods to be sterilized at different heights. Hence, even though the goods are placed at different heights in the chamber, each product in the goods will be subject to a horizontal flow of steam and/or air. Due to the provision of the first heat exchanger, with its surprising cooling and heating effect, even the steam and/or air being diverted from the duct with the first heat exchangers early in the duct, as seen in the flow path, will provide a sufficient cooling or heating effect on the goods to be sterilized.

According to one exemplary embodiment, said partition wall comprises two partition wall elements that are movable in relation to each other, wherein each one of said partition wall elements comprises slots, wherein it is possible to align the two partition wall elements with each other in order to allow a partial or total flow of steam and/or air to be diverted from said flow path and into said space for goods to be sterilized.

This arrangement provides for the possibility to decide whether to allow a partial or total flow of steam and/or air to be diverted from said flow path or not. In situations where it is desired with a horizontal flow of steam and/or air to pass the goods, the slots of each of the two partition wall elements of a partition wall may be aligned with each other and thereby provide a multitude of through holes from the duct where the first heat exchanger is provided to the space for receiving goods. In situations where it is not desired with a horizontal flow, the slots of each of the two partition wall elements may be positioned so that they face the surface of the other partition wall element. By this, the slots will be blocked so that no through-flow is possible through them. In that case, the flow of steam and/or air may exit the duct in which the first heat exchanger is provided through an opening provided between the partition wall and the bottom of the chamber.

According to one exemplary embodiment, it is possible to increase or decrease the amount of fluid that is being diverted from the duct by adjusting the alignment between the slots of the two partition wall elements.

According to one exemplary embodiment, the partition wall elements are configured so that when the slots of them are aligned, one of the partition wall elements blocks the opening provided between the partition wall and the bottom of the chamber of the autoclave. By this, it is possible to ensure, for those applications where a substantially horizontal flow is desired, that the total flow of steam and/or air exits the duct in which the first heat exchanger is provided through the slots in the partition wall.

According to one exemplary embodiment, said autoclave comprises at least two fan arrangements, and wherein a second heat exchanger arrangement is provided for each one of said fan arrangements.

There exist large autoclaves having a multitude of sterilization zones provided in the chamber. In that case, each sterilization zone may have its own fan arrangement and first and second heat exchanger arrangements.

BRIEF DESCRIPTION OF THE DRAWINGS

The present invention will now be described, for exemplary purposes, in more detail by way of embodiments and with reference to the enclosed drawings, in which.

DETAILED DESCRIPTION OF AN EXEMPLARY EMBODIMENT

Figure 1:
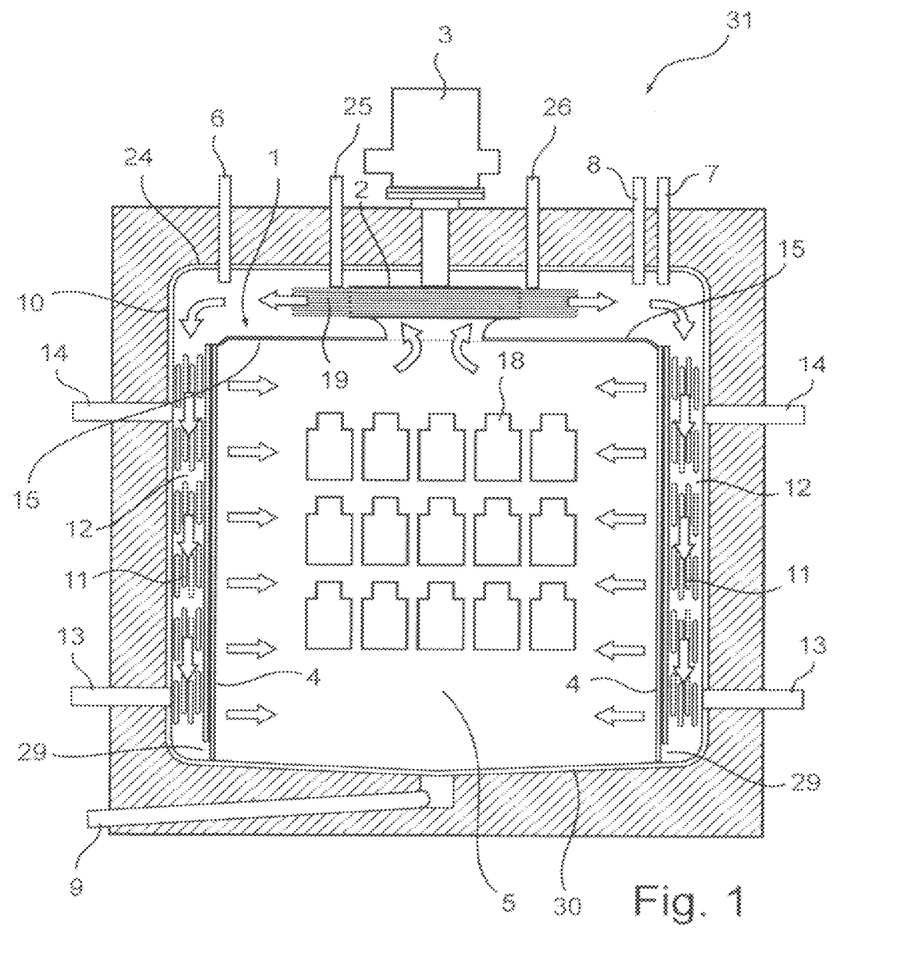
FIG. 1 is a schematic view of an embodiment of a ventilator autoclave, showing the flow path of steam and/or air in said autoclave.
Figure 2:
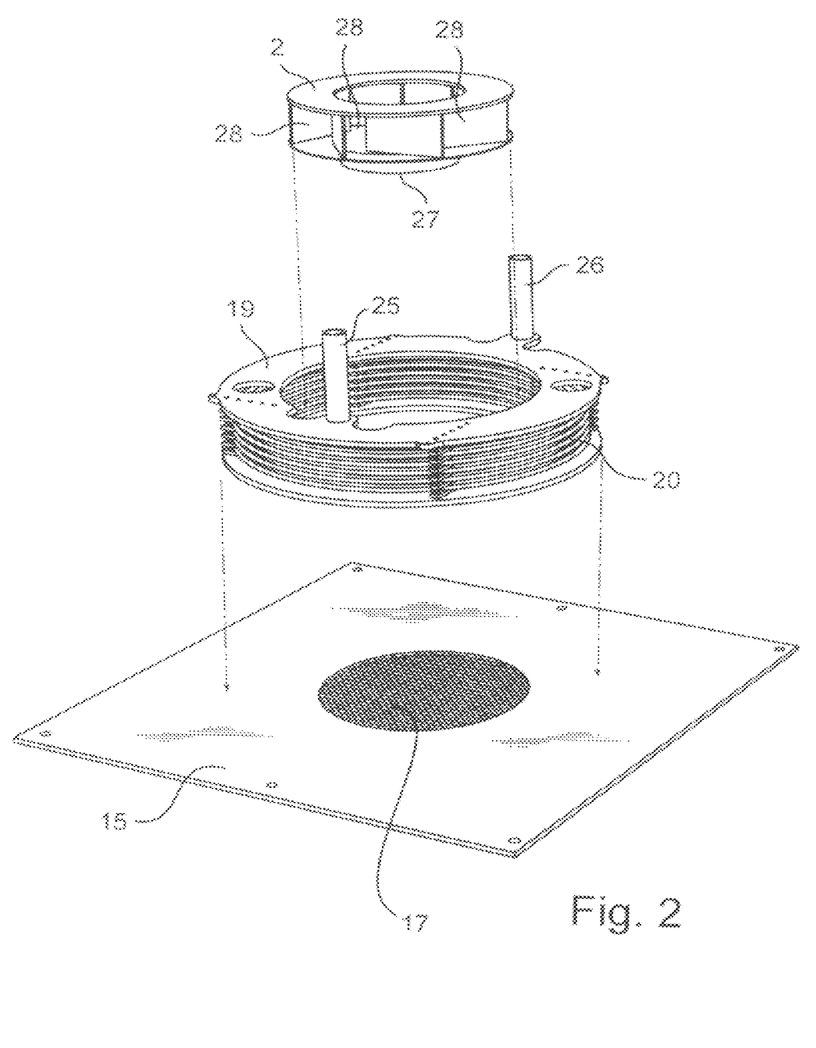
FIG. 2 is a perspective view of an embodiment of the fan arrangement, the second heat exchanger arrangement and the top section of the partition wall.
Figure 3:
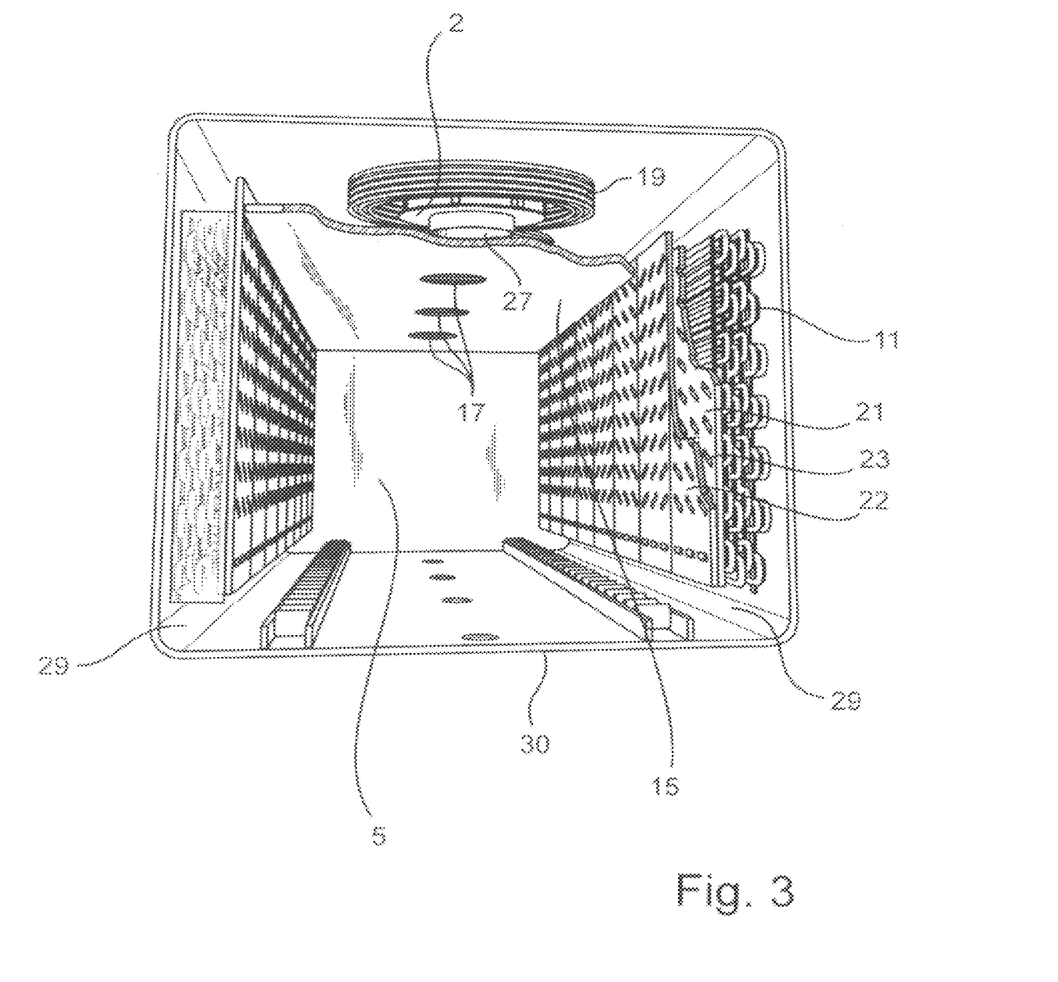
FIG. 3 is a perspective view of an embodiment of a chamber of a ventilator autoclave, with a portion of the partition wall broken away.

FIGS. 1 and 3 shows a steam/air autoclave with a chamber 1. The autoclave 31 is provided with a pipe 7 at the top of the autoclave for supplying steam to the chamber 1, a pipe 8 at the top of the autoclave for supplying air to the chamber 1, and a drainage 9 at the bottom of the chamber 1. In certain embodiments, the steam and air may be supplied through one common pipe, and hence, both of the pipes 7 and 8 are not necessary. The autoclave also comprises a safety valve 6 provided at the top of the autoclave. A stainless steel fan 2 is installed in the ceiling 24 of the chamber. The fan is of centrifugal, or in other words, radial type with an inlet 27 and multiple outlet openings 28, which are best seen in FIG. 2. It is driven by an electric motor 3 via a mechanical seal mounted on top of the autoclave. The fan diameter is in this embodiment typically approximately 50 cm. The purpose of the fan 2 is to circulate a gaseous mixture consisting of steam and/or air in the chamber.

Liners or partition walls 4 are installed within the autoclave chamber 1. The partition walls 4 forms a space 5 for goods 18 to be sterilized in the chamber 1. The partition walls are provided so that a duct in the form of a space 12 is created between each of the outer side walls 10 of the chamber 1 and the partition walls 4. The partition walls 4 leave a respective opening 29 close to the floor 30 of the chamber. First stainless steel heat exchangers 11 are provided in each of the ducts 12. Each of the first heat exchangers 11 comprises interconnected pipes that are connected to respective pipes 13, 14 for supply and discharge of fluid, which may be either cooling fluid or heating fluid. This design ensures, which will be described in greater detail below, that the gaseous mixture is routed in a circulation pattern from the top, down the sides, over the heat exchangers and in contact with the chamber walls, and up through the load, back to the fan inlet. This circulation pattern assures homogeneity and uniformity of temperature distribution.

The partition walls 4 are in this embodiment constituted of two separate partition wall elements 21, 22, provided adjacent each other and being movable in relation to each other. Each of the partition wall elements is provided with a plurality of slots 23. By providing the partition wall elements 21, 22 movable in relation to each other, the slots may be opened or closed depending on whether it is desired to have a horizontal flow of fluid from the ducts 12 to the space 5 or not. Furthermore, by providing the partition wall elements 21, 22 movable in relation to each other, the opening 29 between the partition wall elements and the floor of the autoclave may also be closed. In the disclosed embodiment, the partition wall elements 21, 22 are configured such that one of the partition wall elements 21, 22 blocks the opening 29 when the slots 23 of the partition wall elements 21, 22 are aligned with each other.

A partition wall top section 15 is also provided at a distance from ceiling 24 of the chamber and it comprises at least one grid or net 17. The fan is mounted in the chamber ceiling 24 behind the partition wall top section 15 and fluid in the space 5 may be drawn from the space 5 through the net 17 by the fan 2.

A second heat exchanger 19 is provided adjacent and circumscribing the fan 2, and it is disclosed in greater detail in FIG. 2. In the disclosed embodiment, the second heat exchanger 19 comprises a plurality of spiral-wounded interconnected horizontally provided pipes 20. Heating or cooling liquid may be circulated through the spiral-wounded pipes 20 from an external source (not shown) through the pipes 25, 26 in order to cool or heat the gaseous mixture being circulated in the chamber. The second heat exchanger is provided so that it circumscribes the fan 2. Gaseous mixture that is drawn into the inlet 27 of the radial fan 2 from the chamber 1 and thereafter exits the fan through the openings 28 must pass the second heat exchanger 19. The spiral-wounded interconnected horizontally provided pipes of the second heat exchanger are provided at a distance from each other so that the gaseous mixture may pass through it. The portion of the second heat exchanger that is closest to the periphery of the fan is in the disclosed embodiment provided at approximately 5 cm from the periphery of the fan. The gaseous mixture being discharged from the fan will then have both a tangential and radial velocity component when it passes the second heat exchanger, the benefit of which will be described in greater detail below.

The system will now be described in use and with reference to FIG. 1. Before the sterilization process begins, a start-up process takes place. In the start-up process, goods 18 to be sterilized is placed in the space 5. The doors (not shown) are thereafter closed. The fan engine 3 is started and the fan 2 begins to rotate, thus circulating the air in the chamber 1. Air is then drawn from the space 5 and into the inlet 27 of the fan 2 through the net 17. As the fan 2 rotates, the air is discharged from the openings 28 of the fan and due to the partition walls 4 and the partition wall top section 15, the discharged air moves into the ducts 12 on each sides of the autoclave. Before it enters the ducts 12 it passes the second heat exchanger 19 that is provided in the vicinity of and circumscribing the fan 2. On its way through the ducts 12 the air also passes the respective first heat exchangers 11. In FIG. 1, the slots 23 of the partition wall elements 21, 22 are aligned and the air may exit the duct 12 through the slots. Alternatively, the slots 23 may be closed and the air would then move to the openings 29 provided between the partition walls and the floor 30 of the chamber and re-enter the space 5 through these openings.

Potentially, during this start-up process, either or both of the first and second heat exchangers 11, 19 may be supplied with heated fluid so that the air that passes them becomes heated. By this, the air may then pre-heat the goods to be sterilized to e.g. a temperature of approximately 50-60°, which has proven to be beneficial in terms of avoiding moisture left on the goods after the process has ended.

After the start-up process, the first phase of the sterilization process is initiated. In this phase, steam is introduced in the chamber 1 through the pipe 7. The steam becomes mixed with the air that is being circulated in the chamber 1. The fan 2 is still rotating. The purpose of the steam is to heat the goods 18 to be sterilized to the sterilization temperature, i.e. approximately 121°. Sterile air is also introduced into the chamber through the pipe 8 in order to create a balance between the pressure in the goods to be sterilized and the chamber 1.

In the second phase of the sterilization process, i.e. the actual sterilization phase, the fan 2 may be adjusted to work at a lower speed and the temperature and the pressure in the chamber 1 is maintained at a constant value, i.e. the temperature is kept at the sterilization temperature, while the goods 18 becomes sterilized.

When the goods have been sterilized, the third phase of the sterilization process begins. In this phase, cooling fluid, e.g. chilled water, is being supplied to both the first and second heat exchangers 11, 19 through respective pipes. When the temperature of the products has reached approximately 100°, the fan 2 may, if its speed was reduced during the sterilization phase, once again be made to rotate at a higher speed in order to circulate the gaseous mixture in the chamber 1. As in the first process phase described above, gaseous mixture is drawn from the chamber 5 and into the inlet 27 of the fan 2 through the net 17. As the fan 2 rotates, the gaseous mixture is discharged from the openings 28 of the fan and passes the second heat exchanger 19 that is provided in the vicinity of the fan 2. As mentioned above, due to the speed with which the gaseous mixture is discharged from the openings 28 of the fan, it will have both a tangential and a radial velocity component, as seen in relation to the fan, when it passes the second heat exchanger. Hence, the flow of the gaseous mixture in the vicinity of the fan is, as seen in top view, in a spiral-shaped pattern. This increases the distance that the gaseous mixture is in contact with the second heat exchanger, as compared to a flow with only a radial component. The longer distance the gaseous mixture is in contact with the second heat exchanger is beneficial since it provides for a more effective cooling of the gaseous mixture.

When the gaseous mixture has passed the second heat exchanger and due to the partition walls 4 and the partition wall top section 15, the discharged mixture moves into the ducts 12 on each sides of the chamber. On its way through the ducts 12 the gaseous mixture also passes the first heat exchangers 11 in each duct. As described above, the tangential velocity component decreases as the gaseous mixture moves further away from the fan and due to this, the gaseous mixture moves with substantially only a radial component when it passes the first heat exchangers. In FIG. 1, the slots 23 of the partition wall elements 21, 22 are aligned and the gaseous mixture may exit the duct 12 through the slots. Alternatively, the slots 23 may be closed and the gaseous mixture would then move to the openings 29 provided between the partition walls and the floor 30 of the chamber and re-enter the space 5 through these openings. When the gaseous mixture has entered the space 5 it comes in contact with the goods 18 and cools it.

Due to the slots 23 of the partition wall elements 21, 22 it is possible to decide where the gaseous mixture that has been cooled by the first and second heat exchangers is to enter the space 5. If the partition wall elements 21, 22 are positioned in relation to each other so that the slots 23 are closed, all of the gaseous mixture will exit the ducts 12 and enter the space 5 through the openings 29 provided between the partition walls 4 and the bottom 30 of the chamber 1. Hence, the flow in the space 4 for goods 18 to be sterilized will be substantially vertical. However, if the partition wall elements 21, 22 are positioned in relation to each other so that the slots 23 are open and the opening 29 is closed (as is shown in FIG. 1), the flow of gaseous mixture will exit the ducts 12 and enter the space 5 through the slots. Hence, cooled gaseous mixture will then enter the space 5 at different heights along the height of the autoclave and the flow of gaseous mixture in the space 5 for goods 18 to be sterilized will be substantially horizontal when it passes the goods 18.

The autoclave has been described in relation to an exemplified embodiment. However, several modifications and adaptations are possible within the scope of the present invention as defined in the appended claims.

For example, the autoclave has been described as comprising one zone for containing the goods to be sterilized, one fan, one second heat exchanger and one set of first heat exchangers, each arranged along the respective side walls of the autoclave. However, large autoclaves may contain several sterilization zones in the space 5. It is for example possible with autoclaves comprising one to five sterilization zones. In that case, each sterilization zone may be provided with its own fan, heat exchangers, etc.

Another possible modification is to provide the second heat exchangers along the side walls of the chamber, but before the first heat exchangers in the flow path. In that case, flow of steam and/or air may still have a tangential velocity component when it passes the second heat exchangers.

Furthermore, the second heat exchanger has been described as comprising horizontally arranged pipes that extend circumferentially around the fan in a spiral shape. However, it is also conceivable to use a heat exchanger with e.g. horizontally provided interconnected plates that are provided around the fan.

Furthermore, the slots 23 shown in the drawings have been illustrated as extending at an angle of approximately 45° in relation to the height extension of the side walls of the autoclave. An advantage of this embodiment is that the same sort of carriers for the goods 18 to be sterilized is not always used. If the slots had a horizontal extension, situations may then occur where one or several rows of the slots become blocked by the carriers for the goods to be sterilized. However, it is of course also conceivable with slots being horizontal, vertical or extending at different angles in relation to the height extension of the autoclave.

Furthermore, in the embodiment described above, the opening 29 is closed when the partition wall elements 21, 22 are arranged so that it is possible for the gaseous mixture to pass through the slots 23. However, it is also conceivable to arrange the partition wall elements 21, 22 so that the opening 29 does not become closed when the partition wall elements are arranged to allow a flow through the slots. In such an embodiment, a partial flow of gaseous mixture may exit the duct 12 through the slots 23 and the remaining flow of gaseous mixture may exit through the opening 29.

Furthermore, it is also conceivable with other alternatives regarding the design of the partition walls, e.g. having one fixed partition wall element with or without slots.

The invention claimed is:

1. A ventilator autoclave comprising a chamber with a space for receiving goods to be sterilized, at least one fan arrangement for circulating steam and/or air in said chamber, and at least one first heat exchanger arrangement for cooling and/or heating said steam and/or air, wherein said at least one fan arrangement is arranged and configured to circulate said steam and/or air in said chamber, wherein said chamber is configured such that said steam and/or air that is circulated in said chamber follows a flow path passing at least a part of said at least one first heat exchanger arrangement before reaching said goods to be sterilized wherein said ventilator autoclave further comprises at least one second heat exchanger arrangement that is provided upstream of said at least one first heat exchanger arrangement in said flow path, and wherein said at least one second heat exchanger arrangement is provided at such a distance from the periphery of said at least one fan arrangement that said flow of steam and/or air being circulated by said at least one fan arrangement has a tangential velocity component, as seen in relation to the at least one fan arrangement, when it passes said at least one second heat exchanger arrangement.

2. The ventilator autoclave according to claim 1, wherein said at least one fan arrangement is provided at the ceiling of said chamber.

3. The ventilator autoclave according to claim 1, wherein said ventilator autoclave comprises two first heat exchanger arrangements, which are provided adjacent at least two of said chamber's opposite side walls.

4. The ventilator autoclave according to claim 1, wherein said ventilator autoclave comprises at least one partition wall, wherein said at least one partition wall separates the chamber for receiving goods to be sterilized from the space where said at least one first heat exchanger arrangement is provided.

5. The ventilator autoclave according to claim 1, wherein said at least one second heat exchanger arrangement is provided at the ceiling of said chamber.

6. The ventilator autoclave according to claim 1, wherein said at least one second heat exchanger arrangement is provided so that it circumscribes said at least one fan arrangement.

7. The ventilator autoclave according to claim 1, wherein said at least one second heat exchanger arrangement is provided at a distance of 0-25 cm from the periphery of said at least one fan arrangement.

8. The ventilator autoclave according to claim 1, wherein said at least one second heat exchanger arrangement is provided at a distance from the periphery of said at least one fan arrangement that corresponds to 0-50% of the diameter of said at least one fan arrangement.

9. The ventilator autoclave according to claim 1, wherein said ventilator autoclave comprises partition walls, wherein said partition walls separate the space for receiving goods to be sterilized from the space where said at least one first heat exchanger arrangement is provided, wherein said partition walls are provided with slots, through which a partial or total flow of steam and/or air may be diverted.

10. The ventilator autoclave according to claim 9, wherein said slots are provided at different heights along the partition walls, wherein a partial flow of steam and/or air may be diverted at different heights in said chamber.

11. The ventilator autoclave according to claim 9, wherein said partition walls comprise two partition wall elements that are movable in relation to each other, wherein each one of said two partition wall elements comprises slots, wherein it is possible to align the two partition wall elements with each other in order to allow a partial or total flow of steam and/or air to be diverted from said flow path and into said space for receiving goods to be sterilized.

12. The ventilator autoclave according to claim 1, wherein said ventilator autoclave comprises at least two fan arrangements, and wherein a second heat exchanger arrangement is provided for each one of said at least two fan arrangements.

13. The ventilator autoclave according to claim 1, wherein said at least one second heat exchanger arrangement is provided at a distance of 2-12 cm from the periphery of said at least one fan arrangement.

14. The ventilator autoclave according to claim 1, wherein said at least one second heat exchanger arrangement is provided at a distance of 3-7 cm from the periphery of said at least one fan arrangement.

15. The ventilator autoclave according to claim 1, wherein said at least one second heat exchanger arrangement is provided at a distance from the periphery of said at least one fan arrangement that corresponds to 4-25% of the diameter of said at least one fan arrangement.

16. The ventilator autoclave according to claim 1, wherein said at least one second heat exchanger arrangement is provided at a distance from the periphery of said at least one fan arrangement that corresponds to 6-14% of the diameter of said at least one fan arrangement.

17. The ventilator autoclave according to claim 1, wherein the at least one second heat exchanger arrangement is configured to heat and cool the steam and the air.

18. The ventilator autoclave according to claim 1, wherein the at least one second heat exchanger arrangement is in a form of spiral-wounded pipes.

19. The ventilator autoclave according to claim 18, wherein the spiral-wounded pipes circumscribe the at least one fan arrangement.

20. The ventilator autoclave according to claim 1, wherein the goods are in a form of pre-filled containers containing fluid or formulation.

* * * * *